(12) United States Patent
Moya et al.

(10) Patent No.: US 7,807,823 B2
(45) Date of Patent: *Oct. 5, 2010

(54) METHOD OF FORMING POLYSACCHARIDE STRUCTURES

(75) Inventors: Wilson Moya, Concord, MA (US); Neil P. Soice, Amherst, NH (US); Volkmar Thom, Goettingen (DE)

(73) Assignee: Millipore Corporation, Billerica, MA (US)

( * ) Notice: Subject to any disclaimer, the term of this patent is extended or adjusted under 35 U.S.C. 154(b) by 856 days.

This patent is subject to a terminal disclaimer.

(21) Appl. No.: 11/050,003

(22) Filed: Feb. 3, 2005

(65) Prior Publication Data

US 2005/0220982 A1 Oct. 6, 2005

Related U.S. Application Data

(60) Provisional application No. 60/548,434, filed on Feb. 27, 2004, provisional application No. 60/541,963, filed on Feb. 5, 2004.

(51) Int. Cl.
*C07B 37/02* (2006.01)
*C07H 1/00* (2006.01)

(52) U.S. Cl. ............ 536/51; 536/123.12; 536/124
(58) Field of Classification Search ............ None
See application file for complete search history.

(56) References Cited

U.S. PATENT DOCUMENTS

| | | | |
|---|---|---|---|
| 3,527,712 A | 9/1970 | Renn et al. | |
| 4,274,985 A | 6/1981 | Szejtli et al. | |
| 4,278,790 A * | 7/1981 | McCormick | 536/84 |
| 4,335,017 A | 6/1982 | Miles et al. | |
| 4,452,892 A | 6/1984 | Rosevear | |
| 4,675,104 A | 6/1987 | Rai et al. | |
| 4,743,373 A | 5/1988 | Rai et al. | |
| 4,895,661 A | 1/1990 | Cadotte | |
| 4,935,365 A * | 6/1990 | Nilsson et al. | 435/178 |
| 4,973,683 A * | 11/1990 | Lindgren | 536/120 |
| 5,009,759 A | 4/1991 | Serwer et al. | |
| 5,075,432 A | 12/1991 | Vanzo | |
| 5,277,915 A | 1/1994 | Provonchee et al. | |
| 5,328,603 A * | 7/1994 | Velander et al. | 210/198.2 |
| 5,492,723 A | 2/1996 | Sanderson et al. | |
| 5,672,416 A | 9/1997 | Radola et al. | |
| 5,723,601 A * | 3/1998 | Larsson | 536/103 |
| 5,814,567 A | 9/1998 | Yahiaoui | |
| 5,895,575 A | 4/1999 | Kraus et al. | |
| 5,897,779 A | 4/1999 | Wisted et al. | |
| 5,945,175 A | 8/1999 | Yahiaoui et al. | |
| 6,562,573 B2 | 5/2003 | Halaka | |
| 6,590,096 B1 * | 7/2003 | Berg et al. | 536/55.1 |
| 7,048,858 B2 * | 5/2006 | Ihre | 210/656 |
| 7,214,371 B1 * | 5/2007 | Cohen et al. | 424/93.7 |
| 2003/0155676 A1 | 8/2003 | Lubda et al. | |

FOREIGN PATENT DOCUMENTS

| | | |
|---|---|---|
| EP | 0 222 718 A2 * | 10/1986 |
| EP | 0197784 | 10/1986 |
| EP | 0328256 | 8/1989 |
| EP | 0474617 | 3/1992 |
| EP | 1468723 | 10/2004 |
| EP | 1470854 | 10/2004 |
| WO | WO97/44070 A1 * | 11/1997 |
| WO | WO 00/44928 | 8/2000 |
| WO | WO00/44928 A2 * | 8/2000 |
| WO | WO 00/50160 | 8/2000 |
| WO | WO 03/008078 | 1/2003 |
| WO | WO03/004627 A1 * | 6/2003 |

OTHER PUBLICATIONS

Chaplin, M, "Water Structure and Science," Chapter describing the "Hofmeister Series," Updated Aug. 8, 2007; obtained online at <http://www.lsbu.ac.us/water/index2.html> and <http://www.lsbu.ac.us/water/hofmeist.html>; originally cited in related U.S. Appl. No. 11/050,243.*

Cacace et al., "The Hofmeister Series: Salt and Solvent Effects on Interfacial Phenomenon," Quarterly Reviews in Biophysics, 30(3), 241-277 (Aug. 1997); only abstract supplied; originally cited in U.S. Appl. No. 11/050,243.*

(Continued)

*Primary Examiner*—Lawrence E Crane

(57) ABSTRACT

A process for forming polysaccharide structures such as beads, gel films and porous coatings on porous substrates by forming a room temperature gel-inhibited solution of a polysaccharide, one or more gel-inhibiting agent(s) and a solvent such as water, heating the mixture until all the components are dissolved, cooling the mixture as a solution to about room temperature, forming a three dimensional structure with the solution and adding the structure to a gelling agent to form a polysaccharide gel. Optionally, the solution can be added to a porous structure such as a non-woven fabric or a porous membrane and the solution is allowed to dry before being subjected to the gelling agent. Porous structures having a polysaccharide coating and being capable of convective flow through the pores of the structure and diffusive flow through the coating can be formed.

33 Claims, 4 Drawing Sheets

OTHER PUBLICATIONS

Chaplin, M, "Water Structure and Science," Chapter describing the "Hofmeister Series," Updated Aug. 8, 2007; obtained online at <http://www.lsbu.ac.us/water/index2.html> and <http://www.lsbu.ac.us/water/hofmeist.html>; originally cited in related U.S. Appl. No. 11/050,243.*

Cacace et al., "The Hofmeister Series: Salt and Solvent Effects on Interfacial Phenomenon," Quarterly Reviews in Biophysics, 30(3), 241-277 (Aug. 1997); only abstract supplied; originally cited in U.S. Appl. No. 11/050,243.*

Valle, et al. "Use of Ceramic Monoligths as Stationary Phase in Affinity Chromatography" Biotechnol. Prog. 2003 19, 921-927.

Svec, "Organic Polymer Support Materials" Chromotographic Science Series 2002 87, 2nd Ed., 17-48.

Hamaker, et al. "Rolled Stationary Phases: Dimensionally Strucured Textile Adsorbents for Rapid Liquid Chromatography of Proteins" Ind. Eng. Chem Res 1999, 38, 865-872.

Eveleigh, et al. "Immunochemical Characteristics and Preparative Application of Agarose-Based Immunosorbents" J. Solid-Phase Biochemistry, 1997, 2(1) 45-78.

Shibusawa, "Surface affinity Chromatography of Human Peripheral Blood Cells" J. Chromoatography, 1999, 722(1-2), 71-88.

Striegel et al. "Molecular Characterization of Polysaccharidces Dissolved in ME2NAC-LICL by Gel-Permeation Chromatography" Carbohydrate Research, 1995, 267 (2), 271-290.

* cited by examiner

METHOD OF FORMING POLYSACCHARIDE STRUCTURES

CROSS REFERENCE TO RELATED APPLICATIONS

This application claims the benefit of U.S. Provisional Application No. 60/548,434, filed on Feb. 27, 2004, and of U.S. Provisional Application No. 60/541,963, filed on Feb. 5, 2004. This application is related to the following co-pending and commonly-assigned patent application, which application is incorporated by reference herein, U.S. patent application Ser. No. 11/050,243, entitled "ROOM TEMPERATURE STABLE AGAROSE SOLUTIONS", by Moya et. al., filed on Feb. 3, 2005.

BACKGROUND OF THE INVENTION

Typically in the area of chromatographic separations and electrophoresis gels, polysaccharide polymers such as agarose, are used to make gel media by thermally phase separating the polymer from an aqueous solution. This can be done because these polymers have a melting point and a gel point that is above room temperature, preferably above 30° C.

To process agarose for example, the polymer must be heated above its melting temperature, which is about 92° C., in the presence of water. At that temperature the polymer melts and the molten polymer is then solvated by water to form a solution. The polymer remains soluble in water as long as the temperature is above the polymer's gel point, which is about 43° C. At and below the gel point, the polymer phase separates and becomes a hydrogel that takes on whatever shape the solution was in just before gelling. Additionally, as the agarose approaches its gel point, the viscosity of the solution becomes higher and higher as the hydrogel begins to form.

Traditionally, for electrophoresis gels, the polysaccharide is poured onto a flat substrate and allowed to cool forming a sheet of polysaccharide material on which the electrophoresis process can occur.

For polysaccharide beads, such as are used in chromatography media, the heated solution is kept above its gel point and it is stirred into an immiscible, heated fluid such as mineral or vegetable oil to form beads. The two-phased material (beads of agarose in the immiscible fluid) is then cooled and the beads are recovered. The beads can then be used as is for size exclusion chromatography or further processed by crosslinking, addition of various capture chemistries such as affinity chemistries or ligands, positive or negative charge, hydrophobicity or the like or combinations of crosslinking and chemistries.

Some have tried to use agarose to form a coating on or in a structure rather than as a solid article itself. For instance, according to Cerro et al., Biotechnol. Prog 2003, 19 921-927 (Use of ceramic monoliths as stationary phase in affinity chromatography), thin, surface active only agarose coatings on ceramic monoliths were created by impregnating the monolith with the traditional hot solution of agarose, followed by removal of excess hot agarose solution from the cells within the monolith using compressed air and subsequently cooling the monolith to gel the agarose coating.

One of the major problems with this coating process is that the coatings are difficult to effect on porous materials. In the article mentioned above, the agarose had to be applied in a heated state (thus requiring a substrate that is heat stable). A further problem is that only thin coatings that have only surface activity can be created. In part this may be due to the method used for removing excess agarose. It may also be a function of the agarose gel point and the higher viscosity that occurs as the temperature of the agarose approaches the gel point. Moreover the prior art process is very difficult if not impossible with substrates having pores that are relatively small in comparison to the cell size of the monoliths of the prior art. The reason for these difficulties is that in some cases, air cannot be readily forced through certain porous materials without disrupting or otherwise damaging the porous structure as is the case with certain fabrics or porous membranes. Therefore relatively porous, rigid monolithic structures must be used.

WO 00/44928 suggests forming a temperature stable agarose solution through the use of high levels (e.g. 8M) of chaotropes such as urea. Agarose of this invention is imbibed into a porous support to form a continuous phase. Water is carefully added such that a thin gel layer forms at the interfaces between the agarose solution and the added water. The gel layer prevents migration of the agarose but allows further migration of the water and urea molecules out of the agarose solution into the added water. This process continues until the agarose solution turns into a gel within the interstices of the pores of the porous substrate.

One major problem with this prior art method is that the process by which it is made causes the pores of the substrate to be substantially blocked, severely limiting convective flow through the porous support.

What is desired is a method for making gels, coatings and beads of polysaccharides, especially agarose that overcome the problems of the prior art. More particularly, what is desired is the ability to create coatings on relatively small pored porous articles (0.1-500 microns pore size) that allows for good convective flow through the porous structure with diffusive flow within the agarose itself. Another desire is to form beads and other shaped agarose articles without the need for maintaining high temperatures while doing so.

By using the method of the present invention relatively thick, porous coatings on surfaces can be achieved easily, including the surface of porous materials that are capable of both convective and diffusive flows. Additionally, beads, gels and the like can be formed at or near room temperature.

SUMMARY OF THE INVENTION

The present invention relates to a method of making polysaccharide structures such as coatings, films and beads. More particularly, it relates to making polysaccharide, preferably agarose, structures such as coatings, films and beads at around room temperature.

Using the methods of the present invention one can form polysaccharide structures at room temperature and with controlled gelling of the polymer with polysaccharide polymers that normally gel well above room temperature (about 30° C.). One can coat the surfaces of any article, including irregular materials such as porous materials, including the interior surfaces, with a layer of the polysaccharide polymer without substantially blocking the pores with the polysaccharide so as to allow for convective flow through the porous structure. Additionally, the coating of polysaccharide is thick enough to allow for diffusive flow to occur within the polysaccharide layer itself. Additionally, one is able to form porous polysaccharide beads and gel slabs at or near room temperature.

In one embodiment of the present invention, a room temperature solution of polysaccharide is formed by adding one or more gel-inhibiting materials to a heated solution of polysaccharide in water and cooling the solution to a temperature around room temperature (about 68° F., 20° C.). The solution is formed into a structure of desired shape. The structure is then contacted with a gelling solution and the polysaccharide is allowed to gel. The gelling solution is removed from the formed polysaccharide structure and the formed polysaccharide is washed. Optionally, the formed polysaccharide structure can then be subjected to additional steps such as crosslinking, the addition of capture chemistries and the like.

In another embodiment of the present invention, a room temperature solution of polysaccharide is formed by adding one or more gel-inhibiting materials to a heated solution of polysaccharide that has gel point above that of room temperature, preferably above 30° C. in water and cooling the solution to a temperature around room temperature (about 68° F., 20° C.). The room temperature stable solution is formed into a structure, be it a film or slab, a bead or a coating on a porous substrate. At least a portion of the solvent is evaporated and then the structure is contacted with a gelling solution and the polysaccharide is allowed to gel. The gelling solution is removed from the formed polysaccharide structure and the formed polysaccharide structure is washed. Optionally, the formed polysaccharide structure can then be subjected to additional steps such as crosslinking, the addition of capture chemistries and the like.

In a third embodiment, the room temperature stable polysaccharide solution formed of a polysaccharide, one or more gel-inhibiting agents and a solvent is coated onto a preformed structure such as a porous support and the solvent in the polysaccharide is at least partially evaporated before the polysaccharide is gelled with one or more gelling agents that remove the gel-inhibiting agent. In this embodiment, the optional use of wetting agents such as surfactants helps in forming relatively uniform and continuous coatings.

In a further embodiment, the room temperature stable polysaccharide solution formed of a polysaccharide, one or more gel-inhibiting agents, one or more crosslinking agents and a solvent is coated onto a preformed structure such as a porous support and the solvent in the polysaccharide is at least partially evaporated before the polysaccharide is crosslinked on the structure and is then gelled with one or more gelling agents that remove the gel-inhibiting agent. In this embodiment, the optional use of wetting agents such as surfactants helps in forming relatively uniform and continuous coatings.

In another embodiment, the room temperature stable polysaccharide solution formed of a polysaccharide, one or more gel-inhibiting agents, one or more crosslinking agents, functionalities and a solvent is coated onto a preformed structure such as a porous support and the solvent in the polysaccharide is at least partially evaporated before the polysaccharide solution is crosslinked on the structure and is then gelled with one or more gelling agents that remove the gel-inhibiting agent. In this embodiment, the optional use of wetting agents such as surfactants helps in forming relatively uniform and continuous coatings.

DETAILED DESCRIPTION OF THE INVENTION

The present invention relates to a method of forming a porous polysaccharide structure such as a gel film or slab, a bead or a coating on a porous substrate.

Figure 1:
FIG. 1 shows a block diagram illustrating an embodiment of a process for forming a polysaccharide into a three dimensional structure, according to the present.
Figure 2:
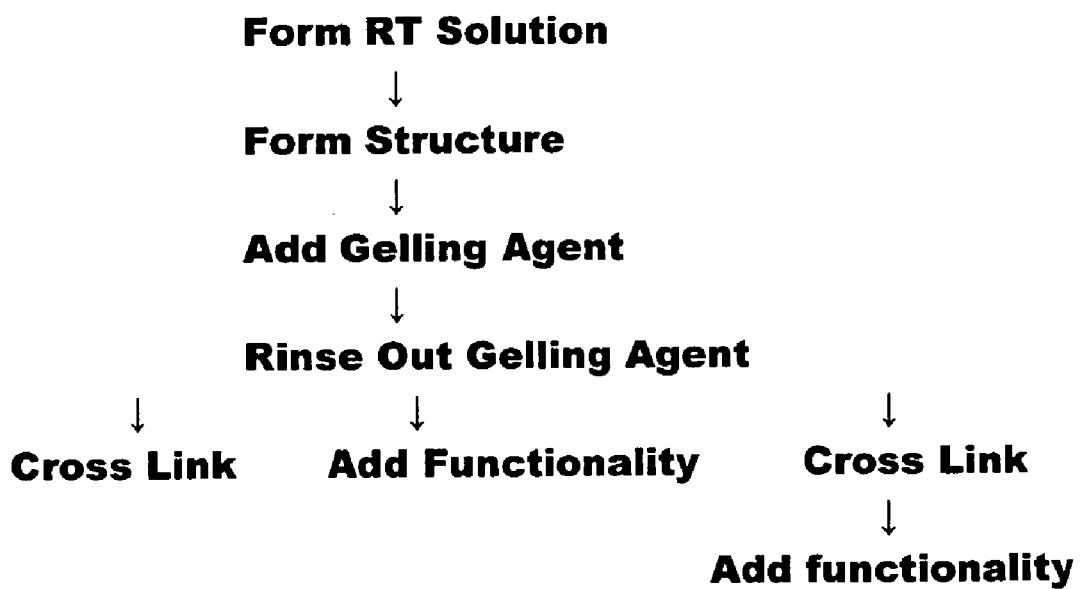
FIG. 2 shows a block diagram illustrating another embodiment of a process for forming a polysaccharide into a three dimensional structure, according to the present invention.

FIG. 1 shows a first embodiment of the process in block diagram fashion. The process comprises the steps of a) forming a room temperature stable polysaccharide solution using a polysaccharide that has a gel point above that of room temperature (20° C.), preferably above 30° C., through the use of gel-inhibiting agent(s), b) forming the polysaccharide into a desired three dimensional structure, c) wetting the structure with a gelling agent that is a non-solvent or poor solvent for the polysaccharide and is a solvent for the gel-inhibiting agent(s), and d) rinsing the structure to remove the gelling agent. Additionally, optional steps include crosslinking the rinsed substrate and/or adding a functionality to the surface of the coating as shown in FIG. 2.

Figure 3:
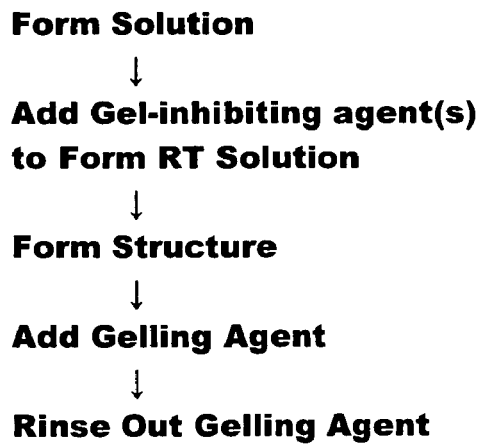
FIG. 3 shows a block diagram illustrating a further embodiment of a process for forming a polysaccharide solution., according to the present invention.
Figure 4:
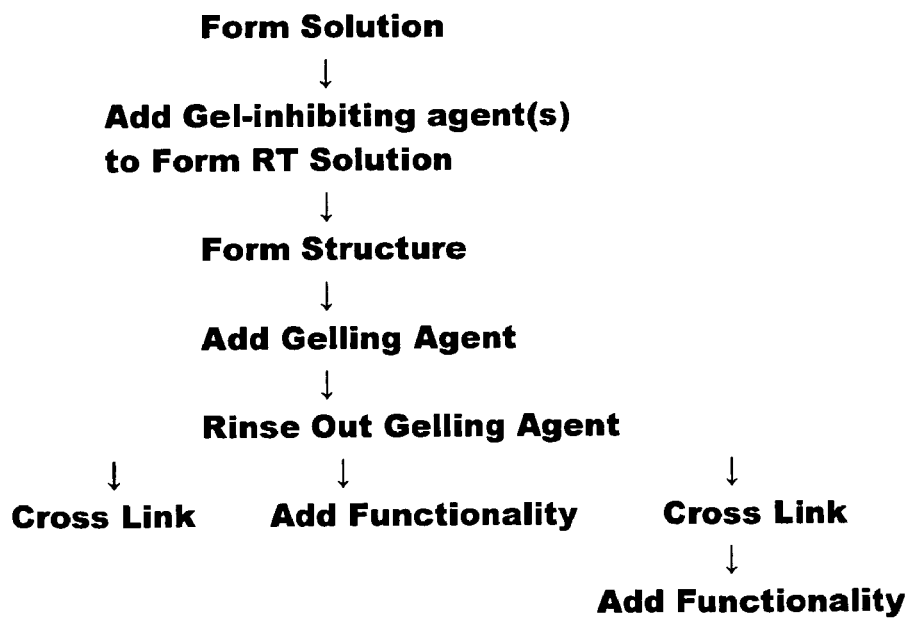
FIG. 4 shows a block diagram illustrating an additional embodiment of a process for forming a polysaccharide solution, according to the present invention.

Alternatively, the process of FIG. 3 may be used to form the room stable solution in block diagram fashion. The process comprises the steps of a) forming a polysaccharide solution without the use of gel-inhibiting agents simply by adding the polysaccharide to a solvent such as water and heating the slurry to a temperature above its melting point (typically about 90° C. and 98° C., most commonly between 92° C. and about 98° C.); the solution is cooled and allowed to gel, the gel-inhibiting agent(s) is then added and dissolved into the solution simply by the action of adding the agent, optionally, the gel is reheated to speed the dissolving of the gel and the gel-inhibiting agent(s); and then cooled to result in a room temperature stable solution, b) forming the polysaccharide solution into a desired three dimensional structure, c) wetting the structure with a gelling agent that is a non-solvent or poor solvent for the polysaccharide and is a solvent for the gel-inhibiting agent(s) and d) rinsing the structure to remove the gelling agent. Additionally, optional steps include crosslinking the rinsed substrate and/or adding a functionality to the surface of the coating as shown in FIG. 4.

Figure 5:
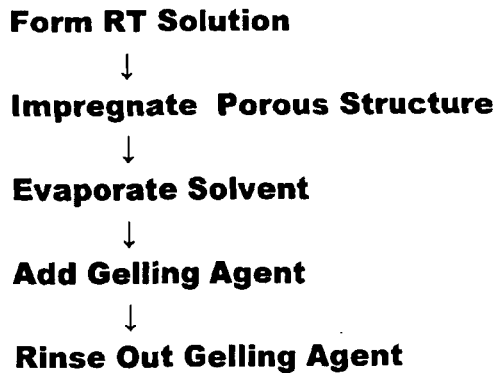
FIG. 5 shows a block diagram illustrating an embodiment of a process for forming a polysaccharide coating on a porous substrate., according to the present invention.
Figure 6:
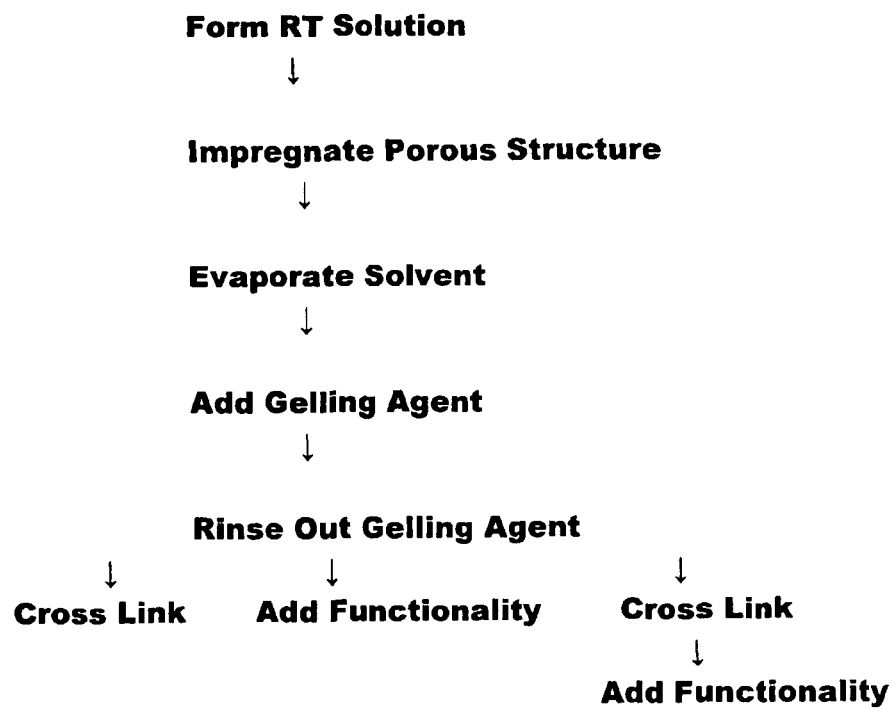
FIG. 6 shows a block diagram illustrating another embodiment of a process for forming a polysaccharide coating on a porous substrate., according to the present invention.

For forming a coating on a porous substrate, the process of FIG. 5 may be used. The process comprises the steps of a) forming a room temperature stable polysaccharide solution through the use of gel-inhibiting agent(s) in a solvent for the polysaccharide at elevated temperatures, b) wetting a porous substrate with that solution, optionally removing excess solution, c) evaporating the solvent from the solution to cause the coating to conform to the surfaces of the substrate, d) wetting the coated substrate with a gelling agent that is a nonsolvent for the polysaccharide and is a solvent for the gel-inhibiting agent(s) and e) rinsing the coated substrate. Additionally, optional steps include crosslinking the rinsed substrate and/or adding a functionality to the surface of the coating as shown in FIG. 6.

Figure 7:
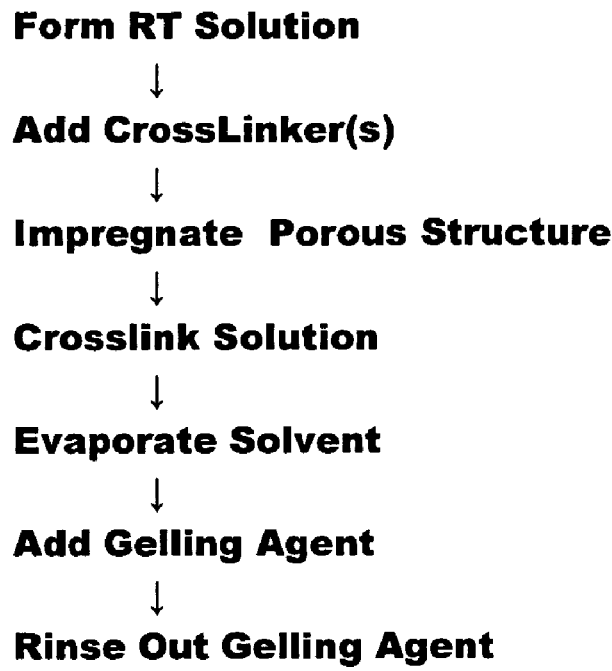
FIG. 7 shows a block diagram illustrating an embodiment of a process for forming a polysaccharide coating on a porous substrate according to the present invention.

An alternative method as shown in FIG. 7 for forming a coating on a porous substrate may be used. The process comprises the steps of a) forming a room temperature stable polysaccharide solution through the use of gel-inhibiting agent(s) in a solvent for the polysaccharide at elevated temperatures, b) adding one or more crosslinking agents to the room temperature stable solution, c) wetting a porous substrate with that solution, optionally removing excess solution, d) crosslinking the coated solution, e) evaporating the solvent from the solution to cause the coating to conform to the surfaces of the substrate, f) wetting the coated substrate with a gelling agent that is a nonsolvent for the polysaccharide and is a solvent for the gel-inhibiting agent(s) and g) rinsing the coated substrate.

Figure 8:
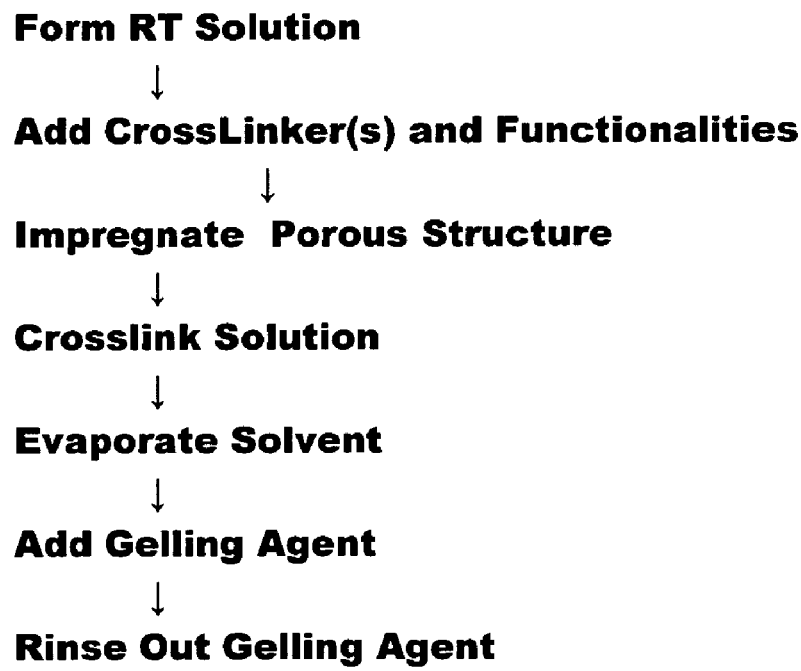
FIG. 8 shows a block diagram illustrating another embodiment of a process for forming a polysaccharide coating on a porous substrate according to the present invention.

An alternative method as shown in FIG. 8 for forming a coating on a porous substrate, the process of FIG. 5 may be used. The process comprises the steps of a) forming a room temperature stable polysaccharide solution through the use of gel-inhibiting agent(s) in a solvent for the polysaccharide at elevated temperatures, b) adding one or more crosslinking agents and functionalities to the room temperature stable solution, c) wetting a porous substrate with that solution, optionally removing excess solution, d) crosslinking the coated solution, e) evaporating the solvent from the solution to cause the coating to conform to the surfaces of the substrate, f) wetting the coated substrate with a gelling agent that is a nonsolvent for the polysaccharide and is a solvent for the gel-inhibiting agent(s) and g) rinsing the coated substrate.

The coating solution is formed of polysaccharide such as agarose, one or more gel-inhibiting agents such as various salts, and one or more solvents such as water for the polysaccharide.

The solution of the above-preferred processes is formed of polysaccharide, such as agarose or other polysaccharides that are not dissolvable at room temperature but will dissolve at higher temperatures and then gel as the temperature falls. This includes most agaroses as well as some dextrans, substituted or cyclodextrans and the like. These materials have a gel point that is above room temperature, generally above 30° C.

Other polysaccharides such as most dextrans and some agaroses that easily dissolve in water at room temperature and do not gel at temperatures above room temperatures or celluloses that do not dissolve at all in water would not need to use the process of the present invention.

The polysaccharide, one or more gel-inhibiting agents and solvent are mixed and heated above the melting point of the polysaccharide. The melting point varies for different grades of polysaccharide, but typically for agarose it is between about 90° C. and 98° C., most commonly between 92° C. and about 98° C. This may be done in one step by combining and heating all three components together. Alternatively, one can first add the polysaccharide in powdered form to a solvent such as water and disperse the powder into a slurry. It is then heated to dissolve the polysaccharide and cooled it to form a gel. The gel is then reheated to a liquid solution and the gel-inhibiting agent is added and dissolved into the solution. Once it has completely dissolved, the solution is cooled, typically to about room temperature (20-23° C.).

In either method, the polysaccharide is dissolved by heating the dispersion in a range of from approximately 90° C. to the boiling temperature. This can be done, for example, in a stirred vessel, or in a microwave oven. The hot solution may be filtered if needed to remove undissolved gel or other particles. Once a clear solution is formed, the solution preferably is allowed to cool.

One may allow this cooling to occur naturally or one may, if desired, affirmatively cool the solution. At room temperature, the solution is a stable, non-gelled solution. The gel point (typically between 30° C. and 68° C.) is suppressed by the addition of the one or more gel-inhibiting agents.

The type of polysaccharide used will be determined by the properties desired of the final coating. The dispersion is made so that the final concentration of polysaccharide is between about 0.1% to about 20%, preferable between about 1% to about 10%, more preferably between about 2% to about 6%, by weight of total final solution.

While water is the preferred solvent for the polysaccharide, a minor amount, up to 20% by weight of the dissolving solution, of co-solvent may be added to improve solubility of the polysaccharide. Examples of suitable co-solvents are dimethylacetamide or dimethylsulfoxide. Others are known to those skilled in the art.

A gel-inhibiting agent is used to prevent the gel from re-gelling after melting and cooling. The agent may be added to the hot solution, or to the solution after cooling to a temperature above the gel point, or at any time prior to complete gelation.

Preferred agents are based on zinc, lithium or sodium salts such as $ZnCl_2$, LiCl, and NaOH. Zinc salts can be used at a concentration of greater than about 15% by weight, based on the dissolving solution, up to the solubility limit, about 45.8% for $ZnCl_2$, and about 54.6% for $Zn(NO_3)_2$. Lithium salts can be used at concentrations greater than about 18%, to their solubility limit, about 45.8% for LiCl, 51.0% for LiNO3, or 54.0% for LiSCN. NaOH can also be used at about 1M concentration. A preferred salt is $ZnCl_2$.

The gel-inhibiting agent may also be a chaotrope, a small solute that enhances the ability of the solvent to dissolve polysaccharides. Non-limiting examples of such gel-inhibiting agents are urea and guanidinium salts at concentrations up to 8M, inorganic salts and buffers such as KI, NaI, $MgCl_2$, potassium dihydrogen phosphate, disodium hydrogen phosphate, tris(hydroxymethyl)aminomethane, sodium tetraborate, and others known to those skilled in the art.

To form a gel film, one simply selects a flat surface such as metal tray or glass plate and spreads the solution over that surface. A gelling agent that is a non-solvent or poor solvent for the polysaccharide and a solvent for the gel-inhibiting agent is then applied to the surface. This can be accomplished by simply sinking the tray or plate into a bath of the gelling agent or by applying a stream or spray of the gelling agent to one or more surfaces of the solution. The gelling agent removes the solvent for the polysaccharide such as water and the gel-inhibiting agent(s) from the solution causing the polysaccharide to gel and form a self-supporting stable structure.

To form a bead, one may simply applies the solution drop wise to a bath of a gelling agent that is a non-solvent for the polysaccharide and a solvent for the gel-inhibiting agent. The gelling agent removes water and the gel-inhibiting agent(s) from the solution causing the polysaccharide to gel as a bead and form a self-supporting stable structure. Alternatively, one can use one or more nozzles that apply the drops to the bath or one may an atomizer to form spray droplets that then contact the bath. In another embodiment, one can use one or more screens spaced apart from each other and located above the bath through which the solution can be fed to form droplets of the desired size. Likewise, one can simply swirl the solution into a bath of gelling agent with sufficient turbulence or with sufficient immiscibility of the polysaccharide that a distinct two-phase fluid is formed with the solution of polysaccharide being the discontinuous phase.

In forming a coating for a porous substrate, the same steps of forming the room temperature stable solution are followed. A porous matrix is then chosen.

The matrix may be a sheet such as a fiber, a series of loose fibers, woven fabrics, non-wovens, mats, felts or membranes or it may be a three dimensional structure such as sponges, poly(HIPES)s or other monolithic structures such as a honeycombs, or porous beads such as a controlled pore glass, porous styrene beads, silica, zirconia and the like. Preferably, the matrix is sheet formed of a woven or non-woven fabric or a membrane.

Non-woven fabrics are flat, porous sheets made directly from separate fibers bonded together by entangling fiber or filaments, thermally or chemically. Typically, nonwoven fabric manufacturers supply media having from 1 to 500 micron mean flow pore (MFP) ratings. For non-woven fabrics, the porous structure is the entangled fibers, and porosity refers to the tortuous spaces between and among the fibers. Porosity has a similar meaning for felted fabrics. A preferred nonwoven is by Freudenberg Nonwovens NA of Lowell, Massachusetts and is type FO2463.

Woven fabrics are produced by the interlacing of warp fibers and weft fibers in a regular pattern or weave style that is at some predefined angle to each other. Typically the weft is at an angle of about 90 degrees to that of the warp. Other commonly used angles include but are not limited to 30, 45, 60 and 75 degrees. The fabric's integrity is maintained by the mechanical interlocking of the fibers cause by the weaving process. Drape (the ability of a fabric to conform to a complex surface), surface smoothness and stability of a fabric are controlled primarily by the weave style, such as plain, twill, satin, basket weave, leno, etc. In this case, the substrate porosity is the space between the fibers and is of a less tortuous nature.

Monoliths are blocks of porous material. They can be rectangular, cylindrical, or foamed into other shapes. Examples are ceramic monoliths, which are ordered structures of packed rectangular or triangular capillaries. These are supplied by Engelhard, Inc. of Huntsville, Ala. and Corning Inc of Corning, N.Y. One form of polymeric monoliths are made from sintered plastic particles by Porex Corporation of Fairbum, Ga.

Poly(HIPES) [high internal phase emulsion] materials are mechanically stable isotropic, open celled polymeric foams. These, and other macroporous polymer structures are described in "Porous polymers and resins for biotechnological and biomedical applications" H.-P. Hentze and M. Antonietti Reviews in Molecular Biotechnology 90 (2002) 27-53.

The matrix may be formed from a variety of materials including glass, plastics, ceramics and metals.

Borosilicate glass is one example of a suitable glass. It can be formed as a fiber, glass mat or porous bead such as the controlled pore glass beads available from Millipore Corporation of Billerica, Mass.

Various ceramics based on the more conventional silicate chemistries or more exotic chemistries such as yttrium, zirconia, titanium and the like and blends thereof can be used. They can be formed into beads, fibers, mats, felts, monoliths or membranes.

Metals include sintered sheets and structures, such as sintered stainless steel or nickel filters, woven screens and non-woven mats, fabrics, fibers and felts such as stainless steel wool.

The preferred substrate is made from plastic, more preferably thermoplastics. Preferred thermoplastics include but are not limited to polyolefins such as polyethylene, polypropylene, sheathed polyethylene/polypropylene fibers, PVDF, polysulfone, polyethersulfones, polyaryllsulfones, polyphenylsulfones, polyvinyl chlorides, polyesters such as polyethylene terephthalate, polybutylene terephthalate and the like, polyamides, acrylates such as polymethylmethacrylate, styrenic polymers and mixtures of the above. Other preferred synthetic materials include celluloses, epoxies, urethanes and the like.

The room temperature stable solution can be used, as is, for coating. It is preferable to add gel-modifying materials to the solution in order to modify and control the structure and properties of the final coating.

One class of added gel modifying materials comprises volatile organics, miscible with the solution. Examples are monohydric alcohols such as methanol, ethanol, and propanols. These can be used up to concentrations that give a slightly cloudy solution. Higher amounts of these alcohols can cause precipitation of the agarose. Preferred amounts are equi-volumetric with the water in the solution, more preferred is to add the alcohols to about 40% to about 60% of the water. A preferred alcohol is methanol. Miscible ketones such as acetone can also be used, but care must be used as the solubility of agarose is less in ketone-water mixtures. Any mixture of two or more of these materials is also contemplated.

Another class of added gel modifying materials comprises non-volatile miscible organics. Non-limiting examples of these included glycerine, ethylene glycol, methyl pentane diol, diethylene glycol, propylene glycol, triethylene glycol, the methyl, ethyl, or n-butyl ethers of ethylene glycol, the dimethyl or diethyl ethers of ethylene glycol, ethylene glycol dimethyl ether acetate ethylene glycol diethyl ether acetate, diethylene glycol methyl ether, diethylene glycol ethyl ether, diethylene glycol n-butyl ether, diethylene glycol dimethyl ether, diethylene glycol diethyl ether, diethylene glycol dimethyl ether acetate, diethylene glycol diethyl ether acetate, N-methyl morpholine, N-ethyl morpholine, and the like. Polyethylene glycols of low molecular weight are also examples of materials that are in this class. Any mixture of two or more of these materials is also contemplated.

Another class of added gel modifying materials comprises water-soluble polymers, which include by way of examples, polyvinyl pyrrolidone, polyvinyl alcohol, polyethylene glycols, dextrans, and water-soluble polyacylamides, including substituted polyacylamides, such as polydimethylacrylamide. These polymers are believed to act as "porogens." That is, they control the amount of volume of the coating that is freely permeable to dissolved solutes when the coated porous substrate is in use.

These polymeric additives can be used as blends with the polysaccharide in the initial dissolution step, or they can be dissolved in the solution with or after the added materials just discussed are mixed. Care must be taken not to add an excessive amount of polymer, as coagulation of the solution may occur. Ratios of polymer to polysaccharide of from about 0.1 to 10 are possible. Preferred polymers are polyvinyl alcohol and dextrans. Polyacrylamides have also been found to be useful.

To obtain optimum coatability of the solution, one or more surfactants are added to the solution. Each combination of solution type and substrate will require some experimentation to determine the optimum type of surfactant. Anionic surfactants have been found to be useful, with anionic fluorosurfactants being preferred. Of these, 3M FC-99 and FC-95 or equivalents from other suppliers are most preferred. These can be used in concentrations of from about 0.001% to about 10%, preferably from about 0.01% to about 5% by total weight of the solution.

The substrate is impregnated with the coating such as soaking the substrate in a bath of the coating, applying the coating material by a doctor blade, spray nozzle, curtain coater, roll coater, extrusion coater or any other method known to one of ordinary skill in the art to apply a coating to a porous substrate. Excess coating material is removed such as by blotting or shaking the coated substrate, squeezing such as through a nip roller, scraping the surface of the coated matrix or by blowing air or a gas at the substrate's surface.

The solvent for the coating is then at least partially removed by evaporation. Preferably, this is a controlled evaporation such that the coating evaporates relatively uniformly throughout the entire substrate. The use of heat warmed air (preferably between 20 and 80° C.); microwave drying, vacuum oven drying and the like to control and/or sped evaporation may be used if desired. This causes a polysaccharide coating to be formed on the substrate surfaces that is dry to the touch, but still contains some residual moisture within it.

The coated substrate is then subjected to a gelling agent that removes the gel-inhibiting agent(s) from the coating and causes the polysaccharide to form a porous hydrogel coating. The gelling agent can be water, if done so as not to overly swell the coating. This can be done by controlling the previous solvent removal/drying step so that the water extracts the gel-inhibiting agents before deleterious swelling can occur. Once a large proportion of the gel-inhibiting agents are removed, swelling in water is reduced to a minimum. The use of water with added salts reduces the tendency of the aqueous rinse to swell the coating.

The use of organic solvents as the gelling agents to remove the gel-inhibiting agent(s) without swelling the coating is preferred. Acetone, methanol, ethanol, or propanols are useful. Mixtures of from about 25% to about 95% acetone or methanol in water have been found to be useful. Similar acetone/methanol mixtures are also useful.

The substrate may be sprayed with the gelling agent, although preferably it is immersed into a bath containing the agent. The agent is preferably applied at room temperature.

The coated substrate is then rinsed with water and maintained preferably in a wet state. This rinsing step is generally done at temperatures between about 15° C. and about 50° C., preferably between 20° C. and 50° C. The coated substrate will have at least a portion of all of its surfaces (facial and interior surfaces) covered with a coating that is permeable to biomolecules. Preferably the coating is relatively uniformly applied to the matrix. More preferably, substantially all of the surfaces are covered by the coating. Also preferably, the coating is of relatively uniform thickness throughout the substrate.

The coating may then be crosslinked if desired by any of the chemistries commonly used in the industry to crosslink materials containing multiple hydroxyl groups, such as polysaccharide beads, these chemistries being as non-limiting examples, epichlorohydrin or other multifunctional epoxy compounds, various bromyl chemistries or other multifunctional halides; formaldehyde, gluteraldehyde and other multifunctional aldehydes, bis(2-hydroxy ethyl)sulfone, dimethyldichloro-silane, dimethylolurea, dimethylol ethylene urea, diisocyanates or polyisocyanates and the like.

It may also have one or more functionalities applied to it, including ligands, such as Protein A or Protein G, natural or recombinatorily derived versions of either, modified versions of protein A or G to render them more caustic stable and the like, various chemical ligands such as 2-aminobenzimidazole (ABI), aminomethylbenzimidazole (AMBI), mercaptoethylpyridine (MEP) or mercaptobenzimidazole (MBI), or various chemistries that render the coating cationic, anionic, philic, phobic or charged, as is well-known in the art of media formation.

Functional groups used in liquid chromatography that are adaptable to the present invention include groups such as, but not limited to, ion exchange, bioaffinity, hydrophobic, groups useful for covalent chromatography, thiophilic interaction groups, chelate or chelating, groups having so called pi-pi interactions with target compounds, hydrogen bonding, hydrophilic, etc.

These groups may be added after the coating has been applied and crosslinked to the substrate or they may be added to the initial solution and the composition of the initial solution is modified accordingly, such as pH being lowered or raised, so that the reaction to link the functional groups to the coating occurs concurrently with the crosslinking reaction (as shown in FIG. 8).

The composite substrate can then be placed into a holder and have a liquid stream (containing one or more desirable components capture in it) run through the composite substrate so that the desired components are separated from the rest of the liquid. Typically, it is the desired components that are captured from the liquid and the rest of the liquid including impurities passes through. Alternatively, the desired components may pass through and impurities can be captured by the media. The composite is washed to remove any unbound materials and then the captured material is eluted using a change in ionic strength, pH or the like.

If desired or required, one may apply a second or even more coating layers to the first in order to reach the desired thickness of coating(s), to change their chemical nature (i.e., layers of different coatings) and the like.

The substrate, even with the coating(s), has high permeability and good flow and capacity characteristics. The matrix is self-supportive and provides a platform or structural network for the coating(s).

It is preferred that the matrix selected be highly porous, so that there is minimal, but sufficient wall or solid material within it to provide the structural integrity and high porosity and flow. The pore sizes may vary from about 5 to about 500 microns, preferably 10 to 300 microns, more preferably from about 50 to about 200 microns and more preferably from 50 to 100 microns, depending upon the fluid and the constituent that is desired to be captured from it. For example, in an application to capture a desired protein from an unclarified, lysed cell broth, the pores of the matrix should be sufficiently large enough to allow good permeability at high flow rates of the broth through the matrix while still allowing for a high level of capture on a single pass, such as greater than 50%. In the above application a pore size of from about 100 to about 300 microns would be preferred. In an application starting with clarified or clean feedstreams, the pore size can be smaller, form about 30 to about 60 microns. For laboratory devices such as syringe filters, or microtiter plates, which are used with a variety of solution conditions, smaller pores are preferred when clean, very dilute solutions are used. These pores are from about $0.1\mu$ to about $10\mu$.

The coating(s) themselves are also porous in nature so that they are permeable to biomolecules. Preferably they are capable of absorbing biomolecules within their bulk, namely within the pores formed within the coating(s). The coating(s) are thick enough to create these pores and have some diffusional flow into them, thereby increasing overall capacity of the structure above that of the surface alone and in some applications selectivity of the capture, but they are sufficiently thin so that the diffusion length is limited and not a negative factor in performance either in capturing or releasing the biomolecules.

The coating(s) typically constitute at least 1% of the total volume of the coated substrate. Preferably they are from about 5% to about 80% of the total volume of the coated substrate.

By another measure, on average, the coatings reduce the average diameter of the substrate pores by an amount from about 1% to about 80%, preferably from about 10% to about 50%, more preferably from about 20% to about 50% from that of the uncoated substrate.

By another measure, the coatings reduce the permeability of the substrate by an amount from about 5% to about 80% of that of the uncoated substrate.

Another method for determining the amount of coatings used is fractional porosity, which is important for ensuring the flow through the coated substrate. Fractional porosity is the ratio of volume within the coated substrate that is available to the solution being processed to the total volume of the coated substrate. A higher fractional porosity gives a higher inherent flow capacity to the coated substrate. For the coated substrates of the present invention, preferred fractional porosities are from about 0.35 to about 0.55.

The coating(s) are generally from about 1 to 100 microns in thickness, preferably from about 2 to about 20 microns in thickness and more preferably from about 5 to about 15 microns in thickness. Thickness refers to the change in the characteristic measure of the solid phase of the substrate. For example, for a woven or non-woven fabric, the change in the radius of the characteristic fiber is the coating thickness. The diameters of pores of the coating(s) may vary within the range of those commonly used in chromatography or from about 1 to about 200 nanometers, preferably from about 1 to about 100 nanometers, more preferably from about 1-50 nanometers. They should be of a size sufficient to allow for the passage or permeation of the desired material into them, such as proteins, DNA or RNA fragments, plasmids or other biomolecules, synthetic molecules such as oligonucleotides, other selected molecules and the like.

In a preferred embodiment the coating covers the surfaces of the substrate to a substantially uniform thickness. To accomplish this requires routine trials in which the coating solution viscosity, substrate pore size, method of removing excess solution and drying procedures are optimized to obtain this end. In general, a practitioner, once aware of the teachings of this invention will determine an approximate coating thickness that will optimize capacity and adsorption and release rates for the desired selected molecule. He will then choose a substrate with a pore size and a porosity such that this thickness will not overly reduce flow. Routine trial and error experimentation, based on the teachings of the present invention, will provide a skilled practitioner a route to the correct formulation and drying method.

In a preferred embodiment, substantially all surfaces are covered with the porous coating, preferably of a uniform thickness.

The structure of the present invention has good hydraulic permeability. Hydraulic permeability is the measure of flow through the media, given as volume flow per facial or frontal area per time, normalized for pressure. Flow is the volume passing through the media per unit time. The present invention has inherent flow even at relatively low pressure (1 psi), and has a stable flow at relatively high flow rates such as 300 cm/hr or greater. Preferably, flow is relatively linear with pressure from about 1 cm/hr to about 500 cm/hr.

The structure also has good capacity. Generally, this means there is a relatively high surface are available to be in direct contact with the fluid flowing through the structure as compared to the surface area of the underlying matrix. Typically, a structure according to the present invention has a surface area that is at least 25%, preferably, 50% and preferably 75% higher than the surface area of the matrix itself so that it is capable of increased breakthrough capacity for the captured materials and allows for faster mass transport (diffusional transport).

Using the polysaccharide solutions and processes of the present invention, films, beads and coatings of the polymer on any surface, including the surfaces of irregular materials such as porous materials, can be effected by applying the solution to the surface of the article followed by the removal of the solvent by evaporation thereby forming a coating of the polymer and the additives. After the formation of the coating is achieved, the additives can be removed such as by extraction with a liquid composition that dissolves the additives but does not affect the agarose thus resulting in a coating of essentially pure agarose. The following examples illustrate the essence of the present invention.

EXAMPLE 1

Room Temperature Stable Agarose Solution Suitable for Coating

Six grams of agarose powder (type XII, obtained from Sigma-Aldrich) were added to 40 grams of water, the mixture was agitated while heating at a temperature of 95° C. until an initial agarose solution was formed. This initial free flowing solution was cooled to room temperature, at which point the solution became a gel having no free flowing characteristics at all. To this gel, 15 grams of zinc chloride were added and the mixture was heated again to 95° C. while agitating until the gel and the salt dissolved to form a homogeneous solution. This solution was then cooled to room temperature; the solution's free flowing characteristics were retained at this temperature. To this solution, 39.9 grams of methanol and 0.1 grams of Fluorad FC-95 fluorosurfactant (3M Company) were added while mixing to form the final agarose solution. This final solution remained liquid at room temperature.

EXAMPLE 2

Coating Using Room Temperature Stable Agarose

A polyolefin non-woven fabric (Type FO2463 from Freudenberg of Lowell, Massachusetts) having a pore size of about 100 microns and a porosity of about 65% was coated with agarose according to the following procedure. The fabric was exposed to the agarose solution of Example 1 such that the fabric was completely wetted by the solution. The wet fabric was then placed between two sheets of polyethylene film and squeezed gently to remove excess solution from the surface of the fabric, the fabric was then removed from the film sheets and allowed to dry at room temperature to remove the methanol and unbound water by evaporation. The dry coated fabric was then immersed in acetone to gel the agarose and to remove the salt and surfactant thus creating the coating of essentially pure agarose. The coated fabric was immersed in water to further rinse the fabric and to remove the acetone, the agarose coated fabric was then kept in water.

EXAMPLE 3

Crosslinking of Agarose Coating

The water-wet agarose coated fabric from example 2 was immersed in a mixture containing 5 grams of epichlorohydrin and 95 grams of 2M sodium hydroxide, the temperature of this mixture was then raised to 50° C. and the crosslinking reaction was allowed to proceed at this temperature for 16 hours under gentle agitation. The crosslinked coated fabric was rinsed with water several times to remove excess reactants and base.

EXAMPLE 4

Functionalization of Crosslinked Agarose Coating with Sulfopropyl (SP) Groups The crosslinked agarose coated fabric of example 3 was immersed in a solution containing 6 grams of sodium bromopropanesulfonate 94 grams of 1M sodium hydroxide, the temperature of this solution was then raised to 50° C. and the functionalization reaction was allowed to proceed at this temperature for 16 hours under gentle agitation. The sulfopropyl functionalized coated fabric was rinsed with water several times to remove excess reactants and base; the fabric was kept in water. The permeability of the modified fabric was measured to be 1.78 $cm^2$/min-psi in a sodium acetate buffer at pH 4.5 and conductivity of 8 mS.

EXAMPLE 5

Protein Binding of SP Functionalized Agarose Coated Fabric

A 13 mm disk of the SP functionalized agarose coated fabric from example 4 was immersed in 6 ml of phosphate buffer at pH 7, conductivity of 2 mS and containing lysozyme in a concentration of 1 g/L, the fabric was allowed to remain in contact with the protein solution for 16 hours at room temperature under agitation. After 16 hours, the concentration of lysozyme in the protein solution was measured and the amount of protein bound to the fabric was calculated based on the volume of the 13 mm disk of fabric. The protein binding capacity of the fabric was measured to be 50 mg lysozyme/ml fabric. The water flow rate through the media was determined by measuring the flow rate through a circular sample of the modified fabric having a diameter of 13 mm and using a column of water 15 cm in height. The sample had a flow rate of water of 50 ml in 14 seconds under these conditions. The uncoated substrate had a flow rate of 50 ml in 6 seconds under the same conditions.

EXAMPLE 6

Making Agarose Beads Using Room Temperature Stable Agarose Solution

The agarose solution of Example 1 was placed in a Badger airbrush (Franklin Park, Ill.) model 250 and the solution was sprayed over an acetone bath under constant stirring. The droplets of agarose solution gelled immediately upon contacting the acetone thereby forming small gel beads, which quickly sank to the bottom of the acetone bath. The beads were then recovered by filtration and were subsequently washed with water several times to remove the acetone. The agarose beads (about 5 microns in diameter) were kept in water.

EXAMPLE 7

Crosslinked Agarose Coating

Six grams of agarose powder (type XII, obtained from Sigma-Aldrich) were added to 40 grams of water, the mixture was agitated while heating at a temperature of 95° C. until an initial agarose solution was formed. This initial free flowing solution was cooled to room temperature, at which point the solution became a gel having no free flowing characteristics at all. To this gel, 15 grams of zinc chloride were added and the mixture was heated again to 95° C. while agitating until the gel and the salt dissolved to form a homogeneous solution. This solution was then cooled to room temperature, the solution's free flowing characteristics were retained at this temperature. The pH of the cooled solution was adjusted to pH 10-14 with NaOH or other base. A suitable crosslinking compound, such as any of the chemistries commonly used in the industry to crosslink materials containing multiple hydroxyl groups, such as agarose, these chemistries being as non-limiting examples, aqueous solution soluble crosslinkers including epichlorohydrin or other multifunctional epoxy compounds, preferably 1,4-butanediol diglycidyl ether or ethylene glycol diglycidyl ether, various bromyl chemistries or other multifunctional halides; formaldehyde, gluteraldehyde and other multifunctional aldehydes, bis(2-hydroxy ethyl)sulfone, dimethyldichloro-silane, dimethylolurea, dimethylol ethylene urea, diisocyanates or polyisocyanates. The crosslinker is then added to about 5% concentration. To this solution, 39.9 grams of methanol and 0.1 grams of Fluorad FC-95 fluorosurfactant (3M Company) were added while mixing to form the final agarose solution. This final solution remained liquid at room temperature.

A polyolefin non-woven fabric having a pore size of about 100 microns and a porosity of about 65% (Type FO2463 from Freudenberg Nonwovens NA of Lowell, Mass.) can be coated according to the following procedure. A coating solution prepared as above is used. The non-woven fabric was exposed to the above coating solution such that the fabric was completely wetted by the solution. The wet fabric was then placed between two sheets of polyethylene film and squeezed gently to remove excess solution from the surface of the fabric, the fabric was then removed from the film sheets and allowed to dry at room temperature. The dry, coated fabric was then placed in an oven at 85° C. for 4 hours to crosslink the agarose. The coated fabric was then rinsed in water several times to remove any unreacted materials. The coated fabric was kept in water.

The invention claimed is:
1. A method of forming porous agarose beads, wherein the agarose has a melting point and a gel point above that of room temperature, comprising the steps of:
   a) providing,
      i) agarose,
      ii) water,
      iii) an effective amount of a gel-inhibiting agent selected from the group consisting of zinc chloride, lithium chloride, sodium iodide, potassium iodide and mixtures thereof,
      iv) a fluorosurfactant, and v.) a gelling agent selected from the group consisting of acetone, methanol, ethanol, propanol and blends thereof, b) combining the agarose, water, and gel-inhibiting agent together to form a mixture, wherein the gel-inhibiting agent is present in concentrations greater than about 15% by weight of the mixture, c) heating the mixture to a temperature above the melting point of the agarose for a time sufficient to dissolve the agarose and the gel-inhibiting agent in the water to form an agarose solution, d) reducing the temperature of the agarose solution to about room temperature wherein the agarose solution is stable at a temperature of about 20° C., and the agarose is present from about 0.1% to about 20% by weight of the agarose solution, e) adding to the agarose solution a fluorosurfactant having a concentration about 0.001% to about 10% by total weight of the solution, f) providing a gelling agent bath, g) applying the agarose solution from step (e) drop wise into the gelling agent bath, thereby forming porous agarose beads, and h) rinsing the porous agarose beads in water to remove the gelling agent and the fluorosurfactant.

2. The method of claim 1 further comprising:
subjecting the rinsed porous agarose beads in step (h) to an additional step (i) of crosslinking the agarose with a cross-linking agent and sufficiently raising the temperature to crosslink the agarose coating, wherein the cross-linking agent is selected from the group consisting of epichlorohydrin, epoxy compounds, halides, bromyl compounds, ethylene glycol diglycidyl ether, formaldehyde, gluteraldehyde, aldehydes, bis(2-hydroxy ethyl) sulfone, dimethyldichloro-silane, dimethylolurea, dimethylol ethylene urea, diisocyanates, polyisocyanates and 1,4-butanediol diglycidyl ether.

3. The process of claim 2 further comprising a step (j) wherein the crosslinked agarose coating is modified by contacting same with sodium bromopropanesulfonate under conditions sufficient to effect addition of propylsulfonate moieties to the agarose surface, and wherein the modified agarose is subsequently contacted with a solution containing lysozyme at about pH 7 to cause further modification of the propylsulfonated agarose surface by the addition of an ionically-associated coating of lysozyme molecules.

4. A process of forming a porous agarose coating on a porous substrate comprising the steps of:
a) providing a mixture including agarose, water, and an effective amount of a gel-inhibiting agent selected from the group consisting of zinc chloride, lithium chloride, sodium iodide, potassium iodide and mixtures thereof in concentrations greater than about 15% by weight of the mixture, b) heating the mixture to a temperature above the melting point of the agarose, for a time sufficient to dissolve the agarose in the water forming an agarose solution, c) reducing the temperature of the agarose solution to about room temperature wherein the agarose solution is stable at a temperature of about 20° C., d) providing a porous substrate, e) wetting the porous substrate with the room temperature stable agarose solution so as to coat all surfaces of the porous substrate, f) evaporating the water from the agarose solution on the porous substrate to form a dry porous agarose coating on the surface of the porous substrate, g) subjecting the dry porous agarose coating on the substrate to a gelling agent selected from the group consisting of acetone, methanol, ethanol, propanol and blends thereof, to remove the gel-inhibiting agent from the agarose coating on the substrate, and h) rinsing the porous agarose coated substrate in water to remove the gelling agent.

5. The process of claim 4 further comprising adding a fluorosurfactant to the agarose solution at the end of step (b).

6. The process of claim 5, wherein the fluorosurfactant is an anionic fluorosurfactant having a concentration about 0.001% to about 10% by total weight of the solution.

7. The process of claim 5 further comprising adding a step (i) to effect the cross linking the porous agarose coating on the substrate at the end of step (h) by adding a crosslinking agent to the agarose coating and sufficiently raising the temperature to form a crosslinked agarose coating, wherein the crosslinking agent is selected from the group consisting of epichlorohydrin, multifunctional epoxy compounds, multifunctional halides, ethylene glycol diglycidyl ether, formaldehyde, gluteraldehyde, multifunctional aldehydes, bis(2-hydroxy ethyl) sulfone, dimethyldichloro-silane, dimethylolurea, dimethylol ethylene urea, diisocyanates, polyisocyanates, and 1,4-butanediol diglycidyl ether.

8. The process of claim 7 further comprising a step (j) wherein the crosslinked agarose coating is modified by contacting same with sodium bromopropanesulfonate under conditions sufficient to effect addition of propylsulfonate moieties to the agarose surface, and wherein the modified agarose is subsequently contacted with a solution containing lysozyme at about pH 7 to cause further modification of the propylsulfonated agarose surface by the addition of an ionically-associated coating of lysozyme molecules.

9. The process of claim 4 wherein the porous substrate is selected from the group consisting of fibers, woven fabrics, non-woven fabrics, felts, mats, open-pored sponges, porous monoliths and porous membranes.

10. The process of claim 4 wherein in step (f) the water is evaporated from the agarose solution on the porous substrate by air movement at a temperature above room temperature but below the melting point of the agarose.

11. The process of claim 4 wherein the gel-inhibiting agent is zinc chloride present in amount of at least 15% by weight of the mixture.

12. The process of claim 4 wherein the gel-inhibiting agent is lithium chloride present in amount of at least 25% by weight of the mixture.

13. The process of claim 4 wherein the gel-inhibiting agent is a mixture of zinc chloride and lithium chloride.

14. A method of forming porous agarose beads comprising the steps of:
a) providing a mixture of agarose and water, b) heating the mixture to a temperature above the melting point of the agarose, for a time sufficient to dissolve the agarose in the water to form an agarose solution, c) reducing the temperature of the agarose solution to about room temperature, d) adding to the agarose solution an effective amount of a gel-inhibiting agent selected from the group consisting of zinc chloride, lithium chloride, sodium iodide, potassium iodide and mixture thereof in concentrations greater than about 15% by weight of the solution, to form an agarose solution stable at a temperature of about 20° C., e) adding to the agarose solution a fluorosurfactant, f) providing a gelling agent bath wherein the gelling agent is elected from the group consisting of acetone, alcohols and blends thereof, g) applying the agarose solution from step (e) drop wise into the gelling agent bath, thereby forming porous agarose beads, and h) rinsing the porous agarose beads in water to remove the gelling agent and the fluorosurfactant.

15. The method of claim 14, wherein the fluorosurfactant is an anionic fluorosurfactant having a concentration about 0.001% to about 10% by total weight of the agarose solution.

16. A method of forming a crosslinked agarose coating on a porous substrate comprising the steps of:

a) providing a mixture of agarose, water, and an effective amount of a gel-inhibiting agent selected from the group consisting of zinc chloride, lithium chloride, sodium iodide, potassium iodide and mixture thereof in concentrations greater than about 15% by weight of the mixture, b) heating the mixture to a temperature above the melting point of the agarose, for a time sufficient to dissolve the agarose in the water forming an agarose solution, c) reducing the temperature of the agarose solution to about room temperature to form a room temperature stable agarose solution stable at a temperature of about 20° C., d) adding a crosslinker selected from the group consisting of epichlorohydrin, multifunctional epoxy compounds, multifunctional halides, ethylene glycol diglycidyl ether, formaldehyde, gluteraldehyde, multifunctional aldehydes, bis(2-hydroxy ethyl)sulfone, dimethyldichloro-silane, dimethylolurea, dimethylol ethylene urea, diisocyanates, polyisocyanates, and 1,4-butanediol diglycidyl ether, to the room temperature stable agarose solution, e) providing a porous substrate, f) wetting the porous substrate with the room temperature stable agarose solution so as to coat all surfaces of the porous- substrate, g) crosslinking under heat the crosslinker and the agarose in the solution coating the substrate resulting in a crosslinked agarose coating on the porous substrate, h) evaporating the water from the crosslinked agarose coating to form a dry crosslinked agarose coating on the porous substrate, i) subjecting the dry crosslinked agarose coating on the coated substrate to a gelling agent selected from the group consisting of acetone, alcohols and blends thereof, to remove the gel-inhibiting agent from the crosslinked agarose coating on the substrate, and j) rinsing the crosslinked agarose coated substrate in water to remove the gelling agent.

17. The method of claim 16, further comprising adding an anionic fluorosurfactant having a concentration about 0.001% to about 10% by total weight of the agarose solution in a step selected from step (b), (c) or (d).

18. A method of forming a crosslinked agarose coating on a porous substrate comprising the steps of:

a) providing a mixture of agarose, water, and an effective amount of a gel-inhibiting agent selected from the group consisting of zinc chloride, lithium chloride, sodium iodide, potassium iodide and mixture thereof in concentrations greater than about 15% by weight of the mixture, b) heating the solution to a temperature above the melting point of the agarose, for a time sufficient to dissolve the agarose in the water forming an agarose solution, c) reducing the temperature of the agarose solution to about room temperature to form a room temperature stable agarose solution stable at a temperature of about 20° C., d) adding to the agarose solution a fluorosurfactant having a concentration about 0.001% to about 10% by total weight of the aqueous solution, e) adding a crosslinker selected from the group consisting of epichlorohydrin, multifunctional epoxy compounds, multifunctional halides, ethylene glycol diglycidyl ether, formaldehyde, gluteraldehyde, multifunctional aldehydes, bis(2-hydroxy ethyl)sulfone, dimethyldichloro-silane, dimethylolurea, dimethylol ethylene urea, diisocyanates, polyisocyanates, and 1,4-butanediol diglycidyl ether to the room temperature stable agarose solution, f) providing a porous substrate, g) wetting the porous substrate with the room temperature stable agarose solution so as to coat all surfaces of the porous substrate, h) crosslinking under heat the crosslinker-room temperature stable agarose solution coating the substrate, i) evaporating the water from the crosslinked agarose coating to form a dry crosslinked agarose coating on the surface of the porous substrate, j) subjecting the dry crosslinked agarose coating on the coated substrate to a gelling agent selected from the group consisting of water, acetone, methanol, ethanol, propanol and blends thereof, to remove the gel-inhibiting agent from the crosslinked agarose coating on the substrate, and k) rinsing the crosslinked agarose coated substrate in water to remove the gelling agent.

19. The method of claim 18, wherein the fluorosurfactant is an anionic fluorosurfactant having a concentration about 0.001% to about 10% by total weight of the agarose solution.

20. A method of forming porous agarose beads comprising the steps of:

a) providing agarose, water, and an effective amount of a gel-inhibiting agent selected from the group consisting of urea, guanidinium salts, zinc chloride, lithium chloride, sodium iodide, potassium iodide and mixtures thereof, b) adding the agarose, the water and the effective amount of the gel-inhibiting agent together to form a mixture such that the agarose is present from about 0.1% to about 20% by weight of the mixture, and the gel-inhibiting agent is present in concentrations greater than about 15% by weight of the solution, c) heating the mixture to a temperature above the melting point of the agarose for a time sufficient to dissolve the agarose and the gel-inhibiting agent into the water to form a first agarose solution, d) reducing the temperature of the a first agarose solution to about room temperature wherein the agarose solution is stable at a temperature of about 20° C., e) adding to the first agarose solution a fluorosurfactant, f) providing a gelling agent bath wherein the gelling agent is selected from the group consisting of acetone, alcohols and blends thereof, g) applying the first agarose solution from step (e) drop wise into the gelling agent bath thereby forming porous agarose beads, and h) rinsing the porous agarose beads in water to remove the gelling agent and the fluorosurfactant.

21. The method of claim 20, wherein the fluorosurfactant is an anionic fluorosurfactant having a concentration about 0.001% to about 10% by total weight of the agarose solution.

22. A method of forming porous agarose beads comprising the steps of:
 a) providing agarose and water;
 b) forming a mixture from the agarose and water;
 c) heating the mixture to a temperature at or above the melting temperature of the agarose to dissolve the agarose in the water;
 d) cooling the first agarose solution to form a gel;
 e) adding to the gel a gel-inhibiting agent selected from urea, guanidinium salts, zinc chloride, lithium chloride, sodium iodide, and potassium iodide in concentrations greater than about 15% by total weight of the gel;
 f) heating the gel and gel-inhibiting agent to form a second agarose solution;
 g) reducing the temperature of the second agarose solution to about room temperature wherein the second agarose solution is stable at a temperature of about 20° C., and the agarose is present from about 0.1% to about 20% by weight of the second agarose solution;
 h) adding to the room temperature second agarose solution an anionic surfactant;
 i) providing a gelling agent bath wherein the gelling agent is elected from the group consisting of acetone, alcohols and blends thereof;
 j) applying the room temperature stable second agarose solution from step (g) drop wise into the gelling agent bath thereby forming porous agarose beads, and
 k) rinsing the porous agarose beads in water to remove the gelling agent and the fluorosurfactant.

23. The method according to claim 22, wherein the gel inhibiting includes urea and guanidinium salts at concentrations up to 8 M.

24. The method of claim 22, wherein the fluorosurfactant is an anionic fluorosurfactant having a concentration about 0.001% to about 10% by total weight of the second agarose solution.

25. A method of forming a porous agarose coating on a porous substrate comprising the steps of:
 a) providing agarose, water, a fluorosurfactant, and a gel-inhibiting agent selected from urea, guanidinium salts, zinc chloride, lithium chloride, sodium iodide, and potassium iodide, wherein the concentration of the gel-inhibiting agent is greater than about 15% by total weight;
 b) forming a mixture of agarose and the water;
 c) heating the mixture to a temperature at or above the melting temperature of the agarose to form a first agarose solution;
 d) cooling the first agarose solution to form a gel;
 e) adding the gel-inhibiting agent to the gel;
 f) heating the gel and gel-inhibiting agent to form a second agarose solution;
 g) reducing the temperature of the second agarose solution to about room temperature wherein the second agarose solution is stable at a temperature of about 20° C., and the agarose is present from about 0.1% to about 20% by weight of the second agarose solution;
 h) adding the fluorosurfactant to the second agarose solution;
 i) providing a porous substrate;
 j) coating the porous substrate with the second agarose solution resulting in a porous agarose coating on the porous substrate; and
 k) subjecting the porous agarose coating on the porous substrate to a gelling agent selected from the group consisting of acetone, methanol, ethanol, propanol and blends thereof, to remove the gel-inhibiting agent from the porous agarose coating on the substrate.

26. The method according to claim 25, further comprising a step prior to step (k) of evaporating the water from the second agarose solution coating the porous substrate to form a dry porous agarose coating on the porous substrate.

27. The method according to claim 26, further comprising a step after step (k) of rinsing the dry porous agarose coating on the porous substrate with water to remove any remaining gelling agent and fluorosurfactant.

28. The method according to claim 25, wherein the gel inhibiting includes urea and guanidinium salts at concentrations up to 8 M.

29. The process of claim 25, further comprising a step of adding a cross linking agent to the porous agarose coating on the porous substrate at the end of step (k), resulting in a crosslinked porous agarose coating on the porous substrate.

30. The process of claim 25, wherein the porous substrate is selected from the group consisting of fibers, woven fabrics, non-woven fabrics, felts, mats, open-pored sponges, porous monoliths and porous membranes.

31. The process of claim 25, wherein the gel-inhibiting agent is lithium chloride present in amount of at least 25% by total weight.

32. The process of claim 25, wherein the gel-inhibiting agent is a mixture of zinc chloride and lithium chloride.

33. The process of claim 25, wherein the fluorosurfactant is an anionic fluorosurfactant having a concentration about 0.001% to about 10% by total weight of the second agarose solution.

* * * * *